United States Patent [19]

Katsumata et al.

[11] Patent Number: 5,605,818
[45] Date of Patent: Feb. 25, 1997

[54] PROCESS FOR PRODUCING L-TRYPTOPHAN, L-TYROSINE OR L-PHENYLALANINE

[75] Inventors: Ryoichi Katsumata, Machida; Masato Ikeda, Hofu, both of Japan

[73] Assignee: Kyowa Hakko Kogyo Co., Ltd., Tokyo, Japan

[21] Appl. No.: 424,621

[22] Filed: Apr. 19, 1995

Related U.S. Application Data

[63] Continuation of Ser. No. 160,810, Dec. 3, 1993, abandoned.

[30] Foreign Application Priority Data

Dec. 3, 1992 [JP] Japan ................................. 4-324105

[51] Int. Cl.⁶ ............................. C12N 1/21; C12P 13/22
[52] U.S. Cl. ................................... 435/108; 435/252.32
[58] Field of Search .......................................... 435/108

[56] References Cited

U.S. PATENT DOCUMENTS

| | | | |
|---|---|---|---|
| 3,787,287 | 1/1974 | Hagino et al. | 435/108 |
| 4,403,033 | 9/1983 | Goto et al. | 435/108 |
| 4,618,580 | 10/1986 | Shiio et al. | 435/108 |
| 4,874,698 | 10/1989 | Ozaki et al. | 435/108 |
| 5,168,056 | 12/1992 | Frost | 435/172.3 |

FOREIGN PATENT DOCUMENTS 0338474  10/1989  European Pat. Off. .
61-260892 11/1986  Japan .

OTHER PUBLICATIONS

Draths et al., J. Am.Chem. Soc. 112:1657–1659 (1990).
Draths et al., J. Am. Chem. Soc. 114:3956–3962 (1992).
Sprenger, J. Bacteriol. 174(5):1707–1708 (1992).
Chen et al., FEMS, Microbiol. Lett. 107:223–230 (1993).
Ikeda et al, Appl. Env. Microbiol 58(3): 781–785 (1992).
WPI Accession No. 87-002443/01 (JP 61-260892), (1986).
Agric. Biol. Chem 53 (8), 2081–2087, 1989, Sugimoto, et al.
Journal Of Bacteriology, Dec. 1969; P. 1289–1295, Josephson, et al.

*Primary Examiner*—Charles L. Patterson, Jr.
*Assistant Examiner*—Eric Grimes
*Attorney, Agent, or Firm*—Antonelli, Terry, Stout & Kraus

[57] ABSTRACT

Disclosed is a process for producing an aromatic amino acid selected from the group consisting of L-tryptophan, L-tyrosine and L-phenylalanine which comprises culturing in a medium a mutant strain of the genus Corynebacterium or Brevibacterium, being capable of producing the aromatic amino acid and also having higher transketolase activity than that of a parent strain thereof until the aromatic amino acid is produced and accumulated in the culture, and recovering the aromatic amino acid therefrom.

3 Claims, 1 Drawing Sheet

PROCESS FOR PRODUCING L-TRYPTOPHAN, L-TYROSINE OR L-PHENYLALANINE

This application is a continuation of Ser. No. 08/160,810, filed Dec. 3, 1993, now abandoned.

BACKGROUND OF THE INVENTION

The present invention relates to a process for producing L-tryptophan, L-tyrosine or L-phenylalanine, by fermentation. L-tryptophan is useful in the medical, food and animal feed industries. L-Tyrosine is useful in the medical industry. L-Phenylalanine is useful in the medical and food industries.

As the microbiological processes for producing such aromatic amino acids using a microorganism belonging to the genus Corynebacterium or Brevibacterium, the following processes have been known so far; for example, a process using a mutant strain to which amino acid auxotrophy and/or resistance to analogs of the aromatic amino acids is/are imparted (Journal of Japan Agricultural Chemistry Association, 50, (1), p.R. 79, 1976), and processes using strains in which activity of a rate limiting enzyme involved in the biosynthetic pathways for the aromatic amino acids has been amplified by the introduction of the genes coding for the rate limiting enzyme (U.S. Pat. No. 4,874,698, and European Publication No. 338,474).

It has been desired to develop a more industrially economical method for the production of L-tryptophan, L-tyrosine or L-phenylalanine.

The present inventors have found that L-tryptophan, L-tyrosine and L-phenylalanine can be produced in a higher yield by intensifying transetolase activity in the aromatic amino acid-producing microorganism belonging to the genus Corynebacterium or Brevibacterium.

Transketolase catalyzes the following two reactions in the pentose phosphate cycle. Transketolase is considered to play an important role in the synthesis or decomposition of erythrose-4-phosphate, which is the initial substrate for the biosynthesis of the aromatic amino acids.

(i) Fructose-6-phosphate+glyceraldehyde-3-phosphate →/← erythrose-4-phosphate+xylulose-5-phosphate (ii) Ribose-5-phosphate+xylulose-5-phosphate →/← glyceraldehyde-3-phosphate+sedoheptulose-7-phosphate

SUMMARY OF THE INVENTION

An object of the present invention is to provide a process for producing an aromatic amino acid selected from the group consisting of L-tryptophan, L-tyrosine and L-phenylalanine, which comprises culturing in a medium a mutant strain belonging to the genus Corynebacterium or Brevibacterium, being capable of producing the aromatic amino acid and also having higher transketolase activity than that of a parent strain thereof until the aromatic amino acid is produced and accumulated in the culture; and recovering the aromatic amino acid therefrom, a DNA fragment containing the transketolase gene; a recombinant DNA containing said DNA fragment; and a microorganism carrying said recombinant DNA.

DETAILED DESCRIPTION OF THE INVENTION

Figure 1:
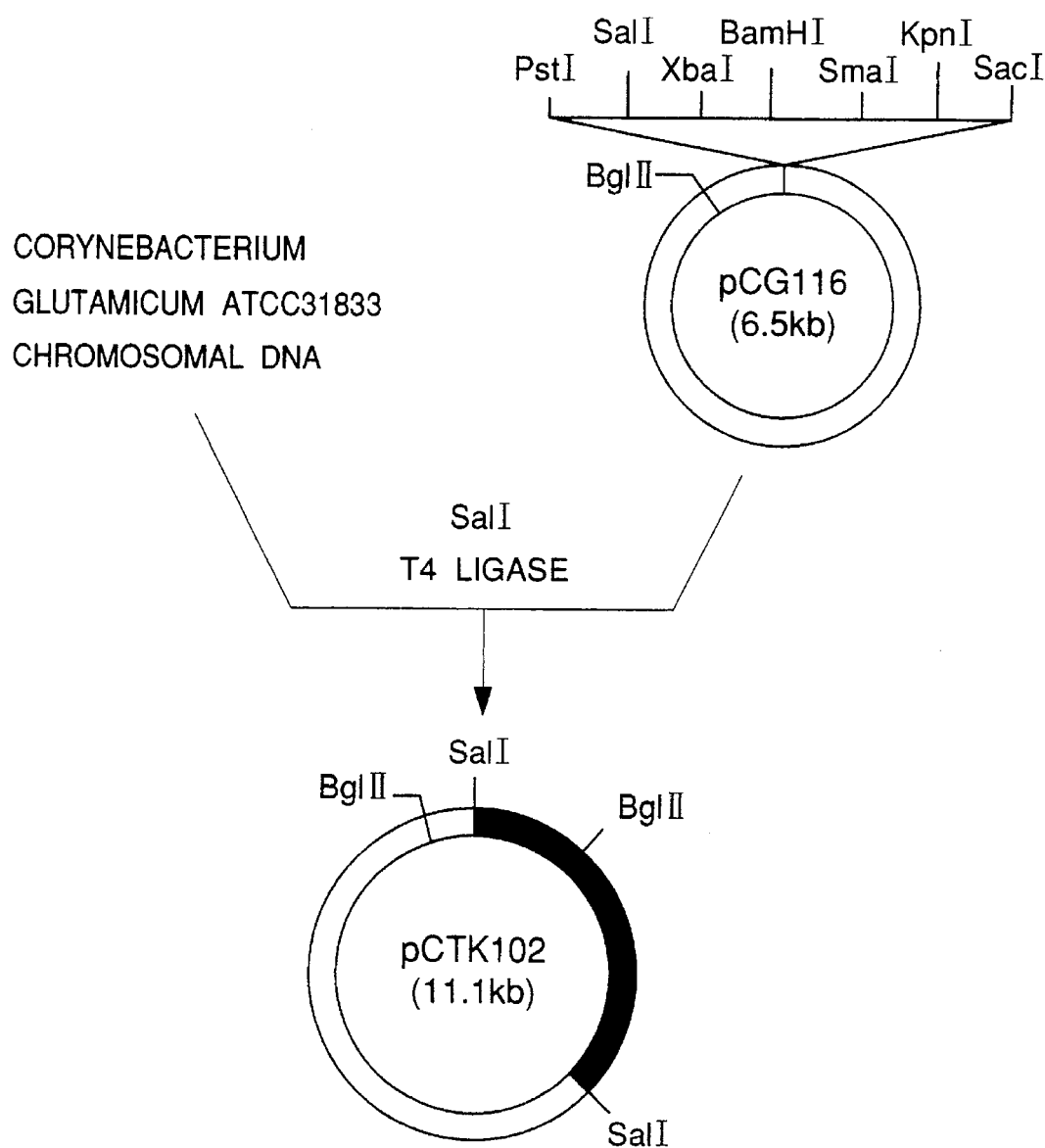
FIG. 1 shows the restriction enzyme cleavage map of plasmid pCTK102 and the construction process for plasmid pCTK102. The bold line of plasmid pCTK102 indicates the DNA fragment containing the transketolase gene cloned from the chromosomal DNA of *Corynebacterium glutamicum* ATCC 31833.

Any mutant strain may be used in the present invention, so long as it belongs to the genus Corynebacterium or Brevibacterium, is capable of producing the aromatic amino acid, and has higher transketolase activity than that of a parent strain thereof.

The mutant strain having higher transketolase activity than that of a parent strain thereof can be obtained either by the conventional mutagenesis such as treatment with N-methyl-N'-nitro-N-nitrosoguanidine and X-ray irradiation, or by the genetically engineering method.

In case of the genetically engineering method, the mutant strain belonging to the genus Corynebacterium or Brevibacterium which has higher transketolase activity than that of a parent strain thereof is obtained by cloning the transketolase gene and introducing the recombinant plasmid carrying the transketolase gene into a host microorganism belonging to the genus Corynebacterium or Brevibacterium by the recombinant DNA techniques.

Any microorganism can be used as the donor source for the transketolase gene, so long as the microorganism possesses transketolase activity. Preferred are genes of bacteria, which are prokaryotes, for example, strains of the genus Escherichia, Corynebacterium, Brevibacterium or Bacillus. *Copynebacterium glutamicum* ATCC 31833 is the most preferred.

The transketolase gene can be cloned by isolating the chromosomal DNA of the donor microorganism, digesting the chromosomal DAN with appropriate restriction enzymes to prepare DNA fragments, ligating the DNA fragments with a vector DNA to prepare a ligation mixture, transforming a shikimic acid auxotrophic recipient with the ligation mixture, selecting shikimic acid prototrophic transformant, and isolating a recombinant DNA containing the transketolase gene from the transformants.

As the vector for cloning the transketolase gene, any plasmid that is autonomously replicable in a strain of the genus *Corynebacterium* or *Brevibacterium* can be used. For Example, plasmids pCG1 (U.S. Pat. No. 4,617,267), pCG2 (U.S. Pat. No. 4,489,160), pCG4, pCG11 (U.S. Pat. No. 4,500,640), pCG116, pCE54, pCB101 (U.S. Pat. No. 4,710, 471), pCE51, pCE52, pCE53 (Molecular and General Genetics 196, 175, 1984) may be used.

A recombinant DNA composed of a vector DNA and a DNA fragment containing the transketolase gene can be obtained as a mixture with various recombinant DNAs according to the ordinary methods, for example, by cleaving the donor DNA and the vector DNA with suitable restriction enzymes followed by, if necessary, treatment of the cleaved ends with a terminal transferase or DNA polymerase, and ligating both DNAs by the action of DNA ligase [Methods in Enzymology, 68 (1979)]. The mixture of ligated DNAs thus obtained is used to transform a shikimic acid auxotrophy (a transketolase deficient recipient) and a transformant in which the deficiency is complemented is selected. The recombinant DNA containing the transketolase gene can be obtained by isolating the plasmid from the transformant.

Any of the strains known as glutamic acid-producing coryneform bacteria may be used as the host microorganism belonging to the genus *Corynebacterium* or *Brevibacterium*. Examples are as follows.

*Corynebacterium glutamicum* ATCC 13032
    *Corynebacterium acetoacidophilum* ATCC 13870
    *Corynebacterium herculis* ATCC 13868
    *Corynebacterium lilium* ATCC 15990
    *Corynebacterium melassecola* ATCC 17965
    *Brevibacterium divaricatum* ATCC 14020
    *Brevibacterium flavum* ATCC 14067
    *Brevibacterium immariophilium* ATCC 14068
    *Brevibacterium lactofermentum* ATCC 13869
    *Brevibacterium thiogenitalis* ATCC 19240

Besides wide-type strains having no ability to produce aromatic amino acids, aromatic amino acid-producing mutants and other known mutants, may be used as the host microorganism.

An aromatic amino acid-producing microorganism belonging to the genus *Corynebacterium* or *Brevibacterium* to be used as the parent strain including a host microorganism in the present invention can be derived from any microorganism which is known as a coryneform glutamic acid-producing bacterium. The aromatic amino acid-producing mutants can be derived from the bacterium by the conventional auxotrophic mutation, aromatic amino acid analog-resistant mutation, or the combination thereof. Also, the aromatic amino acid-producing mutants may also be obtained by introducing a recombinant plasmid containing a gene coding for an enzyme involved in the biosynthesis of the aromatic amino acids into the host microorganism belonging to the genus *Corynebacterium* or *Brevibacterium* by the recombinant DNA techniques. Specifically, the following strains are preferably exemplified.

*Corynebacterium glutamicum* FERM BP-1777
    *Corynebacterium glutamicum* FERM BP-769
    *Corynebacterium glutamicum* ATCC 21571

Introduction of the transketolase gene into a host microorganism belonging to the genus *Corynebacterium* or *Brevibacterium* may be carried out by transforming the host microorganism with the recombinant DNA containing the transketolase gene.

The transformation of the *Corynebacterium* or *Brevibacterium* microorganism with the transketolase gene can be carried out by the method using protoplasts (U.S. Pat. No. 4,683,205).

Moreover, the introduced transketolase gene may be incorporated into the chromosomal DNA of the strain of the genus *Corynebacterium* or *Brevibacterium*, by integrating the recombinant plasmid containing the transketolase gene into the chromosome of the strain, or by substituting its genomic transketolase gene for the transketolase gene having modified promoter in vitro for the high expression of the transketolase gene.

The incorporation of the transketolase gene into the chormosomal DNA may be performed by transformation with a recombinant plasmid which is not replicable in that microorganism (Gene, 107, 61, 1991) or through conjugative transfer of the non-replicable recombinant plasmid from another bacterium wherein the recombinant plasmid is replicable, for example, *Escherichia coli* to the strain of genus *Corynebacterium* or *Brevibacterium* (Bio/Technology, 9, 84, 1991).

Production of an aromatic amino acid using the mutant strain of the genes *Corynebacterium* or *Brevibacterium*, being capable of producing the aromatic amino acid and also having a higher transketolase activity than that of a parent strain thereof, can be carried out by a conventional method for producing amino acids by fermentation. The mutant strain is cultured in a synthetic medium or natural medium containing carbon sources, nitrogen sources, inorganic substances, amino acids, vitamins, etc. under aerobic conditions, while controlling the temperature, the pH, etc.

As the carbon sources, various carbohydrates such as glucose, fructose, sucrose, maltose, mannose, glycerol, starch, starch hydrolysate and molasses; polyalcohols; and various organic acids such as pyruvic acid, fumaric acid, lactic acid and acetic acid may be used. Hydrocarbons and alcohols may also be used depending on the assimilability of the microorganism employed. Preferably, glucose, sucrose and cane molasses are used.

As the nitrogen sources, ammonia; various inorganic and organic ammonium salts such as ammonium chloride, ammonium sulfate, ammonium carbonate and ammonium acetate; urea and other nitrogen-containing organic substances such as peptone, NZ-amine, meat extracts, yeast extracts, corn steep liquor, casein hydrolysates, fish meal or its digested products may be used.

As the inorganic substances, dipotassium hydrogen phosphate, potassium dihydrogen phosphate, magnesium sulfate, sodium chloride, ferrous sulfate, manganese sulfate, calcium carbonate, or the like may be used.

The amino acids and vitamins such as biotin and thiamine may also be added if necessary, depending on the carbon and nitrogen sources contained in the medium. Furthermore, when the mutant strain used requires a specific substance for the growth, it is necessary to add such substance.

Culturing is carried out under aerobic conditions, for example, by shaking culture or by aeration-stirring culture at a temperature in the range of 20° to 40° C. The pH of the medium is preferably maintained around neutrality during the culturing. The aromatic amino acid is accumulated in the culture usually by culturing for one to 5 days. After completion of the culturing, the cells are removed from the culture by filtration or centrifugation, and the aromatic amino acid is recovered from a filtrate or supernatant by a known purification processes involving activated carbon treatment and chromatography with ion-exchanges.

In this manner, by using a *Corynebacterium* or *Brevibacterium* mutant strain which has higher transketolase activity than that of a parent strain thereof, it is possible to produce the aromatic amino acid in a higher yield.

The present invention is further illustrated by the following Examples. The strain construction is exemplified with *Corynebacterium glutamicum*, but the same object also be achieved with the use of other coryneform glutamic acid-producing bacteria.

EXAMPLE

Production of L-tryptophan, L-tyrosine or L-phenylalanine by a strain carrying a recombinant plasmid containing the transketolase gene of *Corynebacterium glutamicum* ATCC 31833.

(1) Preparation of chromosomal DNA of *Corynebacterium glutamicum* ATCC 31833 and vector plasmid pCG116

Twenty milliliters of a seed culture of *Corynebacterium glutamicum* ATCC 31833 which had been grown in an NB medium (a medium consisting of 1 liter of water containing 20 g of bouillon powder, 5 g of yeast extract, with the pH adjusted to 7.2) was inoculated into 400 ml of a semi-synthetic medium SSM [a medium consisting of 1 liter of water containing 20 g of glucose, 10 g of $(NH_4)_2SO_4$, 3 g of urea, 1 g of yeast extract, 1 g of $KH_2PO_4$, 0.4 g of $MgCl_2·6H_2O$, 10 mg of $FeSO_4·7H_2O$, 0.2 mg of $MnSO_4·4-6H_2O$, 0.9 mg of $ZnSO_4·7H_2O$, 0.4 mg of $CuSO_4·5H_2O$, 0.09 mg of $Na_2B_4O_7·10H_2O$, 0.04 mg of $(NH_4)_6Mo_7O_{24}·4H_2O$, 30 μg of biotin and 1 mg of thiamine hydrochloride, with the pH adjusted to 7.2], and cultured by shaking at 30° C. The optical density (OD) at 660 nm (hereinafter, the absorbance was measured at 660 nm unless otherwise specified) was determined with a Tokyo Koden colorimeter. When the OD reached 0.2, penicillin G was added to the culture to a concentration of 0.5 unit/ml. The culturing was further continued until the OD reached 0.6.

The grown cells were collected from the culture, washed with a TES buffer solution [0.03M Tris (hydroxymethyl)-aminomethane (hereinafter referred to as "Tris"), 0.005M disodium ethylenediaminetetraacetic acid (hereinafter referred to "EDTA"), 0.05M NaCl, pH 8.0], and then suspended in 10 ml of a lysozyme solution (25% sucrose, 0.1M NaCl, 0.05M Tris, 0.8 mg/ml lysozyme, pH 8.0), and incubated at 37° C. for 2 hours. The chromosomal DNA was isolated from the collected cells according to the Saito-Miura method (Saito, H. and Miura, K., Biochi. Biophys. Acta, 72, 519, 1963).

Plasmid pCG116, used as a vector, was constructed by ligating a linker obtained from M13mp18 RF DNA (Takara Shuzo Co., Ltd.) with StuI and PstI-digested DNA fragment of pCG11, an autonomously replicable plasmid in *Corynebacterium glutamicum*, utilizing their blunt ends and cohesive ends. The linker is obtained by cleaving M13mp18 RF DNA with *EcoRI*, repairing the cohesive end to blunt end with Klenow fragment (Takara Shuzo Co., Ltd.), and again cleaving the DNA with PstI. Plasmid pCG116 has a molecular size of about 6.5 kb and a single cleavage site for each of BglII, PstI, SalI, XbaI, BamHI, SmaI, KpnI and SacI, and gives a streptomycin- and/or spectinomycin-resistance phenotype.

pCG116 was isolated from cultured cells of *Corynebacterium glutamicum* ATCC 31833 carrying pCG116 according to the procedure described below.

*Corynebacterium glutamicum* ATCC 31833 carrying pCG116 was cultured by shaking in 400 ml of an SSM culture medium at 30° C., treated with penicillin G in the same manner as described above, then suspended in 10 ml of a lysozyme solution and incubated at 37° C. for 2 hours. To the reaction mixture was successively added 2.4 ml of 5M NaCl, 0.6 ml of 0.5M EDTA (pH 8.5) and 4.4 ml of a solution comprising 4% sodium lauryl-sulfate and 0.7M NaCl, the resulting mixture was gently stirred, and then allowed to stand on ice water for 15 hours. The lysate thus obtained was centrifuged at 69,400×g for 60 minutes at 4° C. to recover a supernatant. Then polyethylene glycol (PEG) 6,000 (product of Nakarai Kagaku Yakuhin Co.) was added thereto in an amount of 10% by weight, and the mixture was gently stirred for dissolution and then allowed to stand on ice. After 10 hours, the solution was centrifuged at 1,500×g for 10 minutes to recover the pellet. Five milliliters of a TES buffer solution was added thereto to slowly redissolve the pellet, and 2 ml of 1.5 mg/ml ethidium bromide was added to the solution. Cesium chloride was slowly added thereto until the density of the solution reached 1.580. The solution thus obtained was ultracentrifuged at 105,000×g at 18° C. for 48 hours, and a high-density band at the lower part of the centrifuge tube was detected under ultraviolet irradiation, and withdrawn by puncturing the side of the centrifuge tube using a hypodermic needle, to recover a fraction containing pCG116 plasmid DNA. The fraction was extracted 5 times with an equal volume of an isopropyl alcohols solution comprising 90% by volume of isopropyl alcohol and 10% by volume of TES buffer and further containing a saturated amount of cesium chloride, to remove the ethidium bromide, and then the residue was dialyzed against a TES buffer solution.

(2) Isolation of a transketolase deficient mutant

*Corynebacterium glutamicum* ATCC 31833 was grown at 30° C. in 3 ml of an NB medium until the OD reached about 0.6. The grown cells were collected, washed once with a 50 mM Trismaleic acid buffer solution (pH 6.0), and then treated with 3 ml of the same buffer solution containing 400 g/ml N-methyl-N'-nitro-N-nitrosoguanidine for 20 minutes at room temperature. The treated cells were washed twice by centrifugation with the same buffer solution, and cultured at 30° C. for 1 hour in 3 ml of an NB medium. The culture was diluted to $10^{-5}$–$10^{-6}$ with physiological saline, and then 0.1 ml of the diluted culture was spread on an NB agar medium (an NB medium containing 1.4% agar, pH 7.2), and cultured at 30° C. for 2 days.

The grown colonies were transferred by replica plating on an M1 minimal agar medium [a medium consisting of 1 liter of water containing 10 g of glucose, 1 g of $(NH_4)H_2PO_4$, 0.2 g of KCl, 0.2 g of $MgSO_4·7H_2O$, 10 mg of $FeSO_4·7H_2O$, 0.2 mg of $MnSO_4·4-6H_2O$, 0.9 mg of $ZnSO_4·7H_2O$, 0.4 mg of $CuSO_4·5H_2O$, 0.09 mg of $Na_2B_4O_7·10H_2O$, 0.04 mg of $(NH_4)_6Mo_7O_{24}·4H_2O$, 50 μg of biotin, 2.5 mg of p-aminobenzoic acid, 1 mg of thiamine hydrochloride and 16g of agar, with the pH adjusted to 7.2] and to an M1 agar medium containing 50 g/ml shikimic acid. The strains which did not grow in the former medium but grew in the latter medium were isolated. The transketolase activity in each of the shikimic acid-auxotrophs was determined according to the procedure described below.

A crude enzyme solution was added to a reaction solution comprising 50 mM Tris (pH 7.5), 0.2 mM NADH, 0.01 mM thiamine pyrophosphate, 1 mM $MgCl_2$, 0.5 mM xylulose-5phosphate, 0.5 mM ribulose-5-phosphate, and 20 μg of a mixed solution of glycerol-3-phosphate-dehydrogenase and triose phosphate-isomerase (product of Boehringer Mannheim Co.), of which the total volume was adjusted to 1.5 ml. The reaction proceeded at 30° C. The amount of glycerylaldehyde-3-phosphate produced was determined by the rate of the decrease in the absorbance at 340 nm. As a result, one strain named RA60 was identified as a mutant lacking transketolase activity.

(3) Cloning of a DNA fragment containing the transketolase gene

To 200 μl of a Y-100 reaction solution (10 mM Tris, 6 mM $MgCl_2$, 100 mM NaCl, pH 7.5) containing 1 μg each of the pCG116 plasmid DNA prepared in (1) above and the chromosomal DNA of *Corynebacterium glutamicum* ATCC 31833 was added 20 nits of SalI, and the resulting solution was incubated at 37° C. for 60 minutes. The reaction was stopped by heating at 65° C. for 10 minutes, and 40 μl of a 10-fold concentrated T4 ligase buffer solution (660 mM Tris, 66 mM $MgCl_2$, 100 mM dithiothreitol, pH 7.6), 40 μl of 5 mM ATP, 300 units of T4 ligase (product of Takara Shuzo Co.) and 120 μl of water were added thereto, and the mixture was incubated at 12°C. for 16 hours. The resulting ligase reaction solution was used for the transformation of *Corynebacterium glutamicum* RA60 obtained in (2) above. Four milliliters of a seed culture of *Corynebacterium glutamicum*

RA60 was inoculated into 40 ml of an SSM medium containing 100 μg/ml shikimic acid, and cultured by shaking at 30° C. When OD reached 0.2, the culture were treated with penicillin G and the culturing was further continued until the OD reached 0.6, according to the same method in (1) above. The cells were collected, and then, suspended in 10 m of a solution (pH 7.6) prepared by adding 1 mg/ml lysozyme to an RCGP culture medium [a medium consisting of 1 liter of water containing 5 g of glucose, 5 g of casamino acid, 2.5 g of yeast extract, 3.5 g of $K_2HPO_4$, 1.5 g of $KH_2PO_4$, 0.41 g of $MgCl_2 \cdot 6H_2O$, 10 mg of $FeSO_4 \cdot 7H_2O$, 2 mg of $MnSO_4 \cdot 4-6H_2O$, 0.9 mg of $ZnSO_4 \cdot 7H_2O$, 0.04 mg of $(NH_4)_6Mo_7O_{24}4H_2O$, 30 μg of biotin, 2 mg of thiamine hydrochloride, 135 g of disodium succinate and 30 g of polyvinyl pyrrolidone (molecular weight 10,000)], to a concentration of about 109 cells/ml. The cell suspension was transferred to an L-type test tube and gently shaken at 30° C. for 16 hours to prepare protoplasts. Then, 0.5 ml of the protoplast solution was placed in a small test tube and centrifuged at 2,500×g for 5 minutes to separate the protoplasts. The protoplasts were resuspended in 1 ml of a TSMC buffer solution (10 mM $MgCl_2$, 30 mM $CaCl_2$, 50 mM Tris, 400 mM sucrose, pH 7.5), washed by centrifugation, and then resuspended in 0.1 ml of a TSMC buffer solution. To the suspension was added 100 μl of a mixture of a 2-fold concentrated TSMC buffer solution, and the ligase reaction solution obtained above at a ratio of 1:1. The mixture was mixed with 0.8 ml of TSMC buffer solution prepared by adding 20% PEG 6,000 to a TSMC buffer solution. After 3 minutes, 2 ml of an RCGP culture medium (pH 7.2) was added thereto, and the mixture was centrifuged at 2,500×g for 5 minutes to remove a supernatant. The precipitated protoplasts were suspended in 1 ml of an RCGP medium, and 0.2 ml of the suspension was spread on an RCGP agar medium (a medium prepared by adding 1.4% agar to an RCGP medium, pH 7.2) containing 400 μg/ml spectinomycin, and cultured at 30° C. for 7 days.

The colonies grown on the agar medium were scraped up, washed twice by centrifugation with physiological saline, and then suspended in 1 ml of physiological saline. The suspension was spread on M1 minimal agar medium containing 100 μg/ml spectinomycin, and cultured at 30° C. for 2 days. Transformants having spectinomycin-resistance and shikimic acid-non-auxotrophy were selected.

The plasmid DNA was isolated from the transformants in the same manner as in (1) for the isolation of pCG116. From the restriction enzyme cleavage analysis, one plasmid, isolated from one of the transformants and designated pCTK102, was found to have a structure in which an approximately 4.6 kb SalI DNA fragment had been inserted into the SalI cleavage site within pCG11 (see FIG. 1). Transketolase activity of *Corynebacterium glutamicum* ATCC 31833 and its pCTK102-carrying strain was determined in the same manner as in (2). The transketolase activity of strain ATCC 31833 carrying pCTK102 was at least 10 times as high as that of ATCC 31833. It was confirmed that the transketolase gene was present on the approximately 4.6 kb DNA fragment inserted into pCTK102.

*Corynebacterium glutamicum* K87 (FERM BP-4080) carrying pCTK102 has been deposited in the National Institute of Bioscience and Human Technology (IBHT), Agency of Industrial Science and Technology, Japan as of Nov. 25, 1992, under the Budapest Treaty.

(4) Production of the aromatic amino acids by a pCTK102-carrying strain

Four milliliters of seed cultures of the L-tryptophan-producing *Corynebacterium glutamicum* BPS-13 (FERM BP-1777), the L-phenylalanine-producing *Corynebacterium glutamicum* K52 (FERM BP-769) or the L-tyrosine-producing *Corynebacterium glutamicum* ATCC21571 was each inoculated into 40 ml of an SSM culture medium containing 50 μg/ml L-phenylalanine and 50 μg/ml L-tyrosine and cultured by shaking at 30° C. When OD reached 0.2, the cells were treated with penicillin G and culturing was further continued until OD reached 0.6, in the same manner as in (1). The grown cells were collected, and treated with lysozyme for the preparation of the protoplasts. The resulting protoplasts were transformed with pCTK102 in the same manner as in (3). The plasmid DNA was isolated from the spectinomycin-resistant transformants according to the same manner as in (1). From the restriction enzymes cleavage analysis, it was confirmed that each of the transformants carried pCTK102.

The aromatic amino acid production tests for each of the transformants and the corresponding parent strains were conducted by test tube culture in the following manner.

A 0.5 ml portion of each seed culture which had been cultured by shaking at 30° C. for 24 hours in 3 ml of an S1 seed culture (a culture medium consisting of 1 liter of water containing 20 g of glucose, 15 g of polypeptone, 15 g of yeast extract, 2.5 g of NaCl, 1 g of urea, 200 mg of L-tyrosine and 200 mg of L-phenylalanine, with the pH adjusted to 7.2) and containing 100 μg/ml spectinomycin was transferred to a test tube containing 5 ml of a P1 production medium [a culture medium consisting of 1 liter of water containing 60 g of glucose, 1g of $KH_2PO_4$, 1 g of $K_2HPO_4$, 1 g of $MgSO_4 - 7H_2O$, 20 g of $(NH_4)_2SO_4$, 10 g of corn steep liquor, 10 mg of $MnSO_4$, 30 μg of biotin and 20 g of $CaCO_3$, with the pH adjusted to 7.2] and cultured by shaking at 30° C. for 72 hours. The seed culturing and the culturing in the P1 production medium for the transformants were conducted in the presence of 100 μg/ml of spectinomycin.

After the completion of the culturing, in order to determine the amount of L-tryptophan and L-phenylalanine produced, the culture was filtered to remove the cells. L-tryptophan or L-phenylalanine in the filtrate was assayed by the OPA post column derivation method (Analytical Chemistry, 51, 1338, 1979) using high performance liquid chromatography (HPLC). In order to determine the amount of L-tyrosine produced, L-tyrosine was completely dissolved in the culture by adding 50 μl/ml of a 6N NaOH solution thereto and then heating at 65° C. for 6 minutes. The resulting culture was filtered to remove the cells, and L-tyrosine in the filtrate was assayed in the same manner as described above.

The results are shown in Table 1.

TABLE 1

| Strain | L-tryptophan (g/l) | L-phenylalanine (g/l) | L-tyrosine (g/l) |
| --- | --- | --- | --- |
| BPS-13 | 7.5 | — | — |
| BPS-13/pCTK102 | 8.7 | — | — |
| K52 | — | 6.7 | — |
| K52/pCTK102 | — | 7.6 | — |
| ATCC21571 | — | — | 5.2 |
| ATCC21571/pCTK102 | — | — | 6.1 |

What is claimed is:

1. A process for producing L-trytophan which comprises culturing in a medium *Corynebacterium glutamicum* BPS-13 (FERM BP-1777) carrying a recombinant plasmid pCTK102 comprising a vector plasmid and a DNA fragment consisting of a gene coding for transketolase isolated from a microorganism belonging to the genus *Corynebacterium* or *Brevibacterium*, until the L-tryptophan is produced and accumulated in the culture, and recovering the L-tryptophan therefrom.

2. A process for producing L-phenylalanine, which comprises culturing in a medium *Corynebacterium glutamicum* K52 (FERM BP-769) carrying a recombinant plasmid pCTK102 comprising a vector plasmid and a DNA fragment consisting of a gene coding for transketolase isolated from a microorganism belonging to the genus *Corynebacterium* or *Brevibacterium*, until the L-phenylalanine is produced and accumulated in the culture, and recovering the L-phenylalanine therefrom.

3. A process for producing L-tyrosine, which comprises culturing in a medium *Corynebacterium glutamicum* ATCC21571 carrying a recombinant plasmid pCTK102 comprising a vector plasmid and a DNA fragment consisting of a gene coding for transketolase, until the L-tyrosine is produced and accumulated in the culture, and recovering the L-tyrosine therefrom.

* * * * *